United States Patent [19]

Silvus, Jr.

[11] 4,197,478

[45] Apr. 8, 1980

[54] ELECTRONICALLY TUNABLE RESONANT ACCELEROMETER

[75] Inventor: Howard S. Silvus, Jr., San Antonio, Tex.

[73] Assignee: Southwest Research Institute, San Antonio, Tex.

[21] Appl. No.: 6,285

[22] Filed: Jan. 25, 1979

[51] Int. Cl.$^2$ .............................................. H01L 41/10
[52] U.S. Cl. .................................... 310/316; 310/317; 310/329; 310/325; 310/326; 73/517 R
[58] Field of Search ............... 310/314, 316, 317, 329, 310/321, 325, 326, 328, 332, 331; 340/10; 73/517 R, 517 B

[56] References Cited

U.S. PATENT DOCUMENTS

| | | | |
|---|---|---|---|
| 2,594,841 | 4/1952 | Arndt, Jr. .......................... | 310/316 X |
| 3,336,529 | 8/1967 | Tygart .............................. | 310/321 X |
| 3,447,051 | 5/1969 | Attwood et al. ................. | 310/325 X |
| 3,714,475 | 1/1973 | Baker, Jr. .............................. | 310/321 |
| 3,873,947 | 3/1975 | Johnson ............................ | 310/321 X |
| 3,889,166 | 6/1975 | Scurlock ........................... | 310/325 X |

*Primary Examiner*—Mark O. Budd
*Attorney, Agent, or Firm*—Gunn & Lee

[57] ABSTRACT

An electronically tunable resonant accelerometer is shown wherein the frequency of a resonant peak may be adjusted over a range of frequencies. A piezoelectric element of the accelerometer is used with a seismic mass to generate an output voltage in response to reciprocating motion of the accelerometer. In a compression mode, a feedback loop applies a feedback voltage to a second piezoelectric element mechanically coupled to the first mentioned piezoelectric element. In a cantilever mode, a feedback loop applies a feedback voltage to another location along the first mentioned piezoelectric element which is formed from two bonded piezoelectric elements. By adjusting gain and phase of the feedback loop, first, the resonant frequency of the accelerometer may be varied over a wide range of frequencies to give increased sensitivity to reciprocating motion occurring at a frequency within a narrow band width centered on the resonant frequency, and, second, damping of the resonance may be varied to control the band width of the resonance.

16 Claims, 7 Drawing Figures

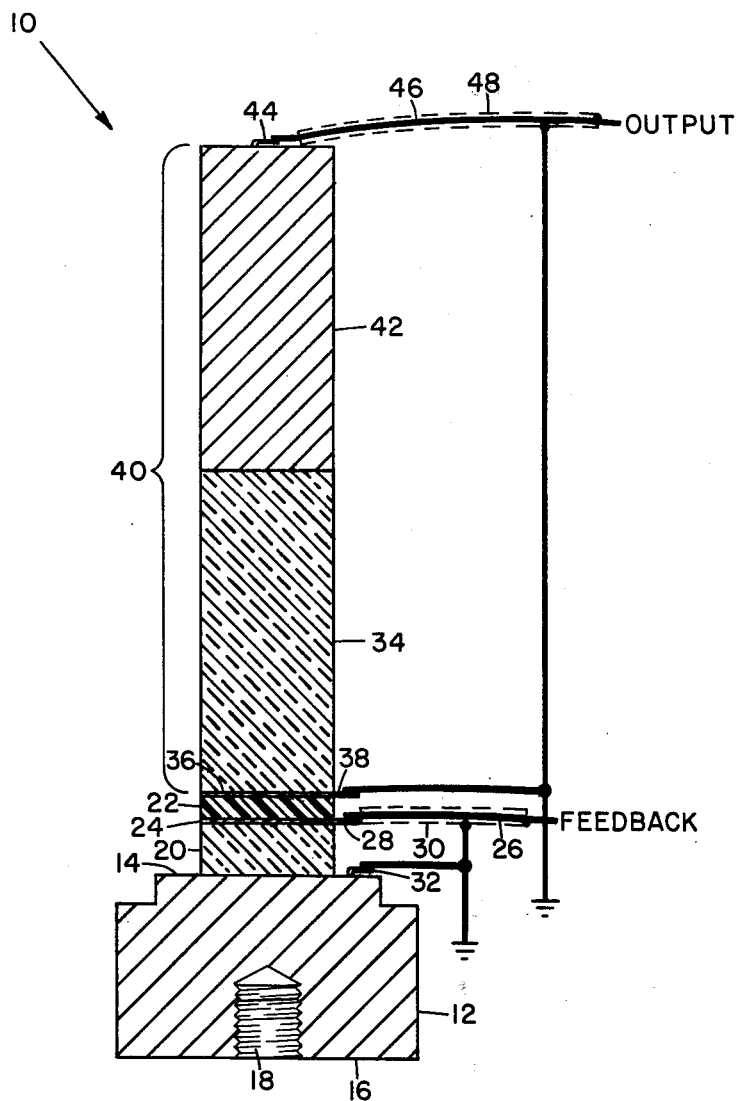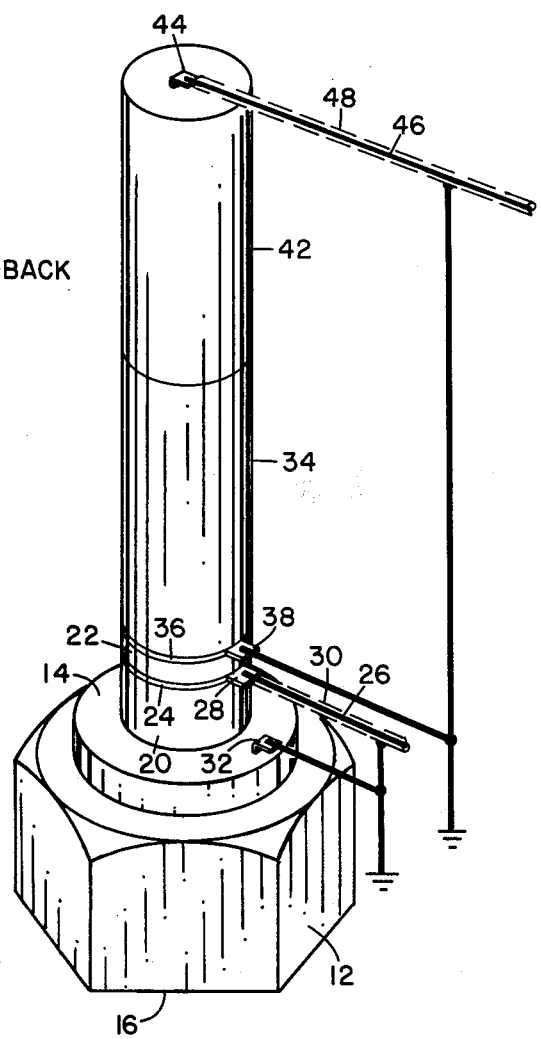

ELECTRONICALLY TUNABLE RESONANT ACCELEROMETER

BACKGROUND OF THE INVENTION

The invention relates to accelerometers and, more particularly, to electronically tunable accelerometers wherein the resonant peak may be varied over a range of frequencies by an appropriate feedback loop having variable gain and phase shift.

BRIEF DESCRIPTION OF THE PRIOR ART

Piezoelectric substances have the ability to transform mechanical energy into electrical energy and, vice versa, to transform an electrical energy into a mechanical energy. Piezoelectric materials are commonly used in microphones and phonograph pickups where mechanical vibrations are transformed into electrical signals of corresponding frequency. Piezoelectric materials are also used in headsets and loud speakers to transform electrical energy into mechanical vibration. An accelerometer using piezoelectric materials is an instrument used for measuring acceleration or for detecting and measuring vibrations.

General purpose piezoelectric accelerometers have flat acceleration response curves with respect to frequency with the low frequency limit being determined by shunt resistance and total shunt capacitance. The high frequency limit for flat response is approximately 20% of the resonant frequency of the accelerometer. In certain cases, the signal of interest may be contained within a relatively narrow band width around a center frequency. To most effectively transduce signals of this nature using a conventional accelerometer, it is necessary to select an accelerometer having a resonant frequency of approximately five times the center frequency of the signal to be converted. Since the sensitivities of general purpose accelerometers are proportional to the inverse square of resonant frequency, a substantial sacrifice in potentially available sensitivity must be made if the conventional accelerometer is utilized. However, a conventional accelerometer could be discarded, and the accelerometer designed to operate at a resonant frequency equal to the center frequency of the narrow band width. At the resonant frequency of the accelerometer, a substantial increase in the sensitivity will result.

Normally it is not practical to utilize conventional fixed frequency, general purpose piezoelectric accelerometers in the resonant mode because the center frequency of the signal of interest in all probability will not coincide with a resonant frequency of any commercially available accelerometer. Furthermore, the exact center frequency of the signal of interest may not be known in advance. Even further, the actual resonant frequency of the accelerometer is dependent upon mounting conditions. It is not practical to fabricate a special fixed resonant frequency accelerometer for each requirement. Because the damping of commercially available piezoelectric accelerometers usually is not controlled during manufacturing, the sensitivity and band width at the top of the resonant peak are not predictable nor repeatable from one accelerometer to another.

Tunable accelerometers have been developed in the past; however, they do not have the simplicity and ease of operation of the present accelerometer. Methods used to vary the resonant frequency of piezoelectric accelerometers have included in the past (1) varying the seismic mass of the accelerometer by displacement of a dense liquid, such as mercury, (2) varying the seismic mass of the accelerometer by electroplating metal from one electrode, isolated from the vibrating system, to another electrode incorporated in the vibrating system, and (3) mechanically varying the unsupported length of a cantilever bender element. Tuning of an accelerometer by mechanical adjustment makes it impractical to tune the accelerometer from a remote location. Electroplating consumes significant quantities of electrical energy to accomplish tuning, has corrosion problems, and at best tunes very slowly.

Some work has been done with electromechanical feedback systems for low frequency seismographs. An example is contained in *Proceedings of the I.R.E.*, "Inert Seismograph Design - Limitations in Principal and Practice (or How Not to Build a Sensitive Seismograph)", Molten & Johnson (November 1962). A complication of the electromechanical feedback systems of the above identified reference was the electromagnetic suspension which required a relatively high static current just to support the weight of the sensor components. Only a small modulation of that high static current was required to achieve the desired feedback. Noise and draft constituted significant development obstacles.

SUMMARY OF THE INVENTION

It is an object of the present invention to provide an electronically tunable accelerometer having a resonant frequency variable over a range of frequencies.

It is another object of the present invention to have an electronically tunable resonant accelerometer with a pair of mechanically coupled piezoelectric elements with a feedback through one of the elements controlling the resonant frequency of the accelerometer.

In an electronically tunable accelerometer wherein the resonant frequency may be varied over a range of frequencies, a preamplifier magnifies the output signal from the accelerometer. A feedback loop supplies an electrical feedback signal derived from the output signal to one of a pair of mechanically coupled piezoelectric elements. By varying the magnitude and phase of the feedback signal, the resonant frequency of the accelerometer is varied with one piezoelectric element either counteracting dimensional changes of the other piezoelectric element to increase the resonant frequency or aiding dimensional changes of the other piezoelectric element to decrease the resonant frequency. By varying the amount of feedback, the resonant frequency of the accelerometer can be set to any desired frequency within an operating frequency range.

Assume that the accelerometer is being used to monitor frequency X of a particular machine having rotating motion. Frequency X would normally represent one of the harmonics created by the machine wherein vibrations of frequency X would occur if the machine was beginning to malfunction. A typical reason for such malfunction may be worn bearings. By having an electronically tunable resonant accelerometer that has an adjustable resonant frequency range including frequency X, the accelerometer can be tuned by varying the gain and phase of the feedback loop to set the resonant peak of the accelerometer at frequency X. Because of the increased sensitivity at the resonant frequency, the accelerometer could detect the early stages of mechanical vibration that would normally occur at frequency X and indicate possible machine malfunction.

The principle of an electronically tunable resonant accelerometer can be described in qualitative terms using the mechanical equivalent of a compression mode accelerometer. The mechanical equivalent comprises a seismic mass supported by a spring (representing the piezoelectric element) with a mechanical input applied to the free end of the spring. The resonant frequency ($f_0$) is determined by the magnitude of the spring constant (k) and the seismic mass (m) according to the following formula:

$$f_0 = 1/2\pi\sqrt{k/m}$$

Such a resonant accelerometer can be tuned by changing either mass, spring constant, or both. The present invention alters the spring constant by inserting an electromechanical feedback device between the driven end of the spring and the mechanical driving source. The electromechanical feedback device is normally a second piezoelectric element designed to change its thickness in response to an applied electric signal.

Assume that a force is applied to the accelerometer thereby causing the spring (which represents a first piezoelectric element) to compress. The feedback signal to a second piezoelectric element will cause the second piezoelectric element to either compress or extend for the desired amount of compensation. If the first spring compresses and the second piezoelectric element extends, the resonant frequency is increased. Reduction in the amount of deflection of the first spring has the same effect as increasing the spring constant (k) thereby increasing the resonant frequency. The degree of which the compression of the first piezoelectric element (first spring) is counteracted by the second piezoelectric element depends upon the gain of the feedback loop.

The generating element of the electronically tunable resonant accelerometer comprises a seismic mass and a first piezoelectric element. The generating element is tightly coupled mechanically to a second piezoelectric element normally much smaller in thickness. The electrical output of the generating element passes through a preamplifier to the output. In addition, the output is fed through a band pass filter, gain control, inverter and phase shifter back to the second piezoelectric element for applying the feedback signal thereto. Mechanical vibrations in the feedback element are coupled to the generating element. By way of the feedback signal, the second piezoelectric element responds in proportion to the output of the generating element thereby completing the feedback function. The feedback signal is applied to the second piezoelectric element can increase (or decrease depending upon the feedback polarity) the resonant frequency of the generating element over an operating frequency range of the accelerometer. Thus, the resonant frequency, sensitivity and band width can be adjusted to give a tunable accelerometer including the desired frequency range of applied motion.

BRIEF DESCRIPTION OF THE DRAWINGS

FIG. 1 is an elevated cross-sectional view of the mechanical portion of an electronically tunable resonant accelerometer in a compression mode.

FIG. 2 is a perspective view of the electronically tunable resonant accelerometer in a compression mode as shown in FIG. 1.

DESCRIPTION OF THE PREFERRED EMBODIMENT

Figure 3:
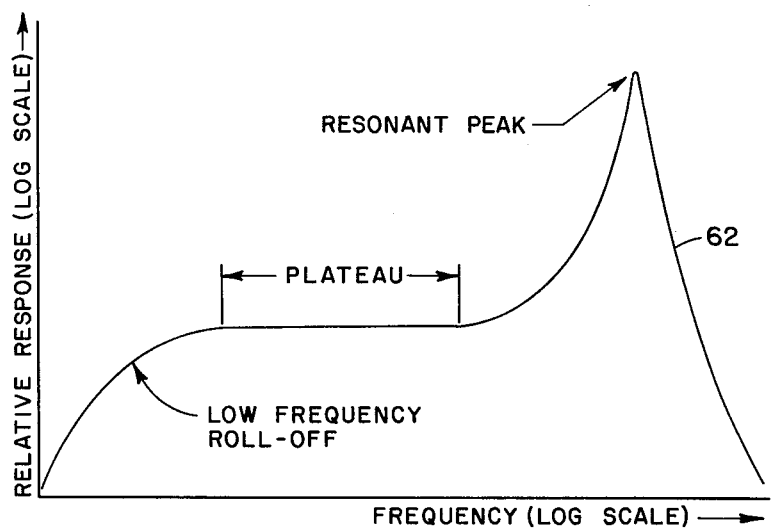
FIG. 3 is a chart of relative response versus frequency of a typical fixed piezoelectric accelerometer.

Referring to FIGS. 1 and 2 in combination, there is shown an accelerometer represented generally by reference numeral 10. The lower end of the accelerometer 10 has a metallic base 12 which may be constructed from any suitable conductive material, such as steel. The metallic base 12 has an upper plane 14 and lower plane 16. In the lower plane 16, a threaded hole 18 is provided which may be used for mounting of the accelerometer 10 on a vibrating surface. Other types of connections between the metallic base 12 and the vibrating surface may be used without varying from the scope of the present invention.

Bonded to the upper plane 14 is a first piezoelectric element 20, which may at various times hereinafter be referred to as the "feedback element". The bonding agent just mentioned (and as will be mentioned hereinbelow) may be of any suitable bonding compound, such as epoxy, and does not necessarily have to be conductive. The first piezoelectric element 20 is basically wafer-shaped with parallel upper and lower surfaces. Connected to the upper surface by the bonding agent is an insulator 22 with a suitable connecting disc 24 inserted therebetween. The connecting disc 24 is a very thin wafer between the abutting surface areas of the insulator 22 and the first piezoelectric element 20. The connecting disc 24 must be of suitable conductive material so that a feedback line 26 may be electrically connected to connecting tab 28. Shielding 30 is electrically connected to metallic base 12 via a soldering tab 32 and to ground.

The insulator 22 is basically wafer-shaped with parallel upper and lower surfaces. The insulator 22 electrically separates first piezoelectric element 20 and second piezoelectric element 34. Inserted between insulator 22 and second piezoelectric element 34 is another connecting disc 36 having connecting tab 38 extending therefrom. Again, the insulator 22 is bonded to the second piezoelectric element 34 by a suitable bonding agent with the connecting disc 36 being inserted therebetween. The second piezoelectric element 34 is part of a generating element 40 which includes a seismic mass 42 bonded to the upper surface of the second piezoelectric element 34. The second piezoelectric element 34 is considerably thicker than the first piezoelectrical element 20, and likewise has parallel upper and lower surfaces. The seismic mass 42 must be a fairly dense conductive material, such as tungsten. On the upper surface of the seismic mass 42 is a soldering tab 44 to which an output line 46 is connected. Shielding 48 for output line 46 is connected to connecting tab 38 of connecting disc 36 and to ground. To prevent any problems with ground loop currents, grounds for shielding 48 and shielding 30 are provided in the electronic controls which will hereinafter be described.

Figure 4:
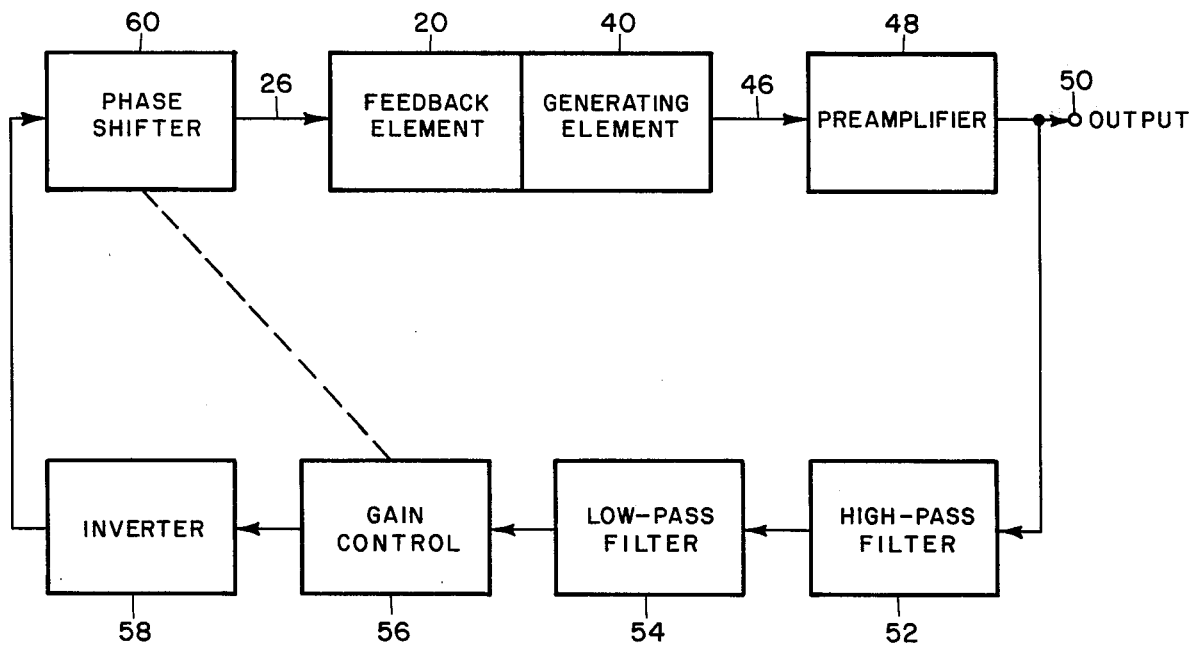
FIG. 4 is a functional block diagram of the electronically tunable resonant accelerometer.

Referring now to FIG. 4, the schematic block diagram shows the feedback element 20 (first piezoelectric element) mechanically coupled to the generating element 40 (second piezoelectric element 34 and seismic mass 42). Any electrical output of the generating element 40 connects through output line 46 to preamplifier 48. The preamplifier 48 amplifies the electrical signal to give an amplifier output at output terminal 50. The preamplifier 48 is a high input impedance, low noise, feedback stabilized circuit which increases the output signal of the generating element 40 to a greater level.

A feedback loop from the output terminal 50 includes a high pass filter 52 that eliminates potentially unstable points at frequencies beyond the tuning range of the accelerometer 10. A low pass filter 54 is used to shape an open loop gain curve at frequencies above the zero feedback resonant frequency of the accelerometer 10, and attenuate the second and higher resonant peaks to less than unity gain thereby eliminating them as potential sources of instability.

As an explanation of open loop gain, if the feedback loop were broken immediately prior to the feedback element 20, and an electrical driving signal from an oscillator were applied to the feedback element 20, output voltage and phase angle could be measured as functions of frequency at feedback line 26. Such measurements will indicate existence of a primary resonant peak characteristic of spring-mass vibrating systems. As is the case in all distributed constant vibrating systems, there are a number of other secondary resonant peaks at higher, but not necessarily harmonically related, frequencies. Near the primary resonant frequency and at many higher frequencies, open loop phase angle passes through zero. At many of the zero crossings of the phase angle, loop gain is greater than unity. If the loop gain is greater than unity and phase angle is zero, closing of the feedback loop will cause the system to oscillate at the phase zero crossing frequency at which the greatest open loop gain exists. Thus, in prior systems, the gain control had to be set for a low gain so that oscillation did not occur. The limiting of loop gain restricts the available tuning range.

The output from the low pass filter 54 is fed to gain control 56 which feeds an output through inverter 58 to phase shifter 60. The gain control 56 is mechanically coupled to the phase shifter 60 as will be described in more detail subsequently. The output of the phase shifter 60 drives the feedback element 20 through feedback line 26 with mechanical vibrations of the feedback element 20 being proportional to the signal received from the phase shifter 60. Mechanical vibrations of the feedback element 20 are mechanically coupled into the generating element 40 to oppose dimensional changes of the generating element 40 thereby increasing resonant frequency.

In a mechanical equivalent of the accelerometer 10, the second piezoelectric element 34 is considered as a mechanical spring. Therefore, the resonant frequency ($f_0$) is determined by the spring constant (k) of the second piezoelectric element 34 and the seismic mass (m) according to the previously mentioned formula:

$$f_0 = 1/2\pi\sqrt{k/m}$$

By having a first piezoelectric element 20 connected to the end of the second piezoelectric element 34 opposite from the seismic mass 42, an electrical signal can be fed back to the first piezoelectric element 20 (feedback element). For example, if the second piezoelectric element 34 is compressed, the first piezoelectric element 20 may be caused to extend, which in mechanical equivalence is the same as increasing the stiffness of the spring or the spring constant (k). The increasing of the spring constant (k) increases the resonant frequency ($f_0$). Therefore, by varying the gain of a feedback loop to the feedback element 20, the resonant frequency ($f_0$) may be tuned over a range of frequencies.

Referring now to FIG. 3, a typical response curve over a range of mechanical frequencies for a piezoelectric accelerometer is shown. The curve 62, which is shown on vertical and horizontal logarithmic scales, has a low frequency roll-off below which the accelerometer cannot be utilized. In prior devices, the plateau of a piezoelectric accelerometer was the normal range of operation. The resonant peak was normally undesirable and attempts to attenuate the resonant peak were commonly used in prior piezoelectric accelerometers to hopefully extend the frequency range of the plateau. However, in the present device by use of the feedback loop and the feedback element 20, the resonant peak is adjusted over a frequency range. At the resonant peak, the sensitivity of an accelerometer is much greater than it is in the plateau region. Therefore, if a given frequency is being monitored, and the resonant peak of the accelerometer is set for that frequency, a much greater sensitivity will result at the monitored frequency.

Figure 5:
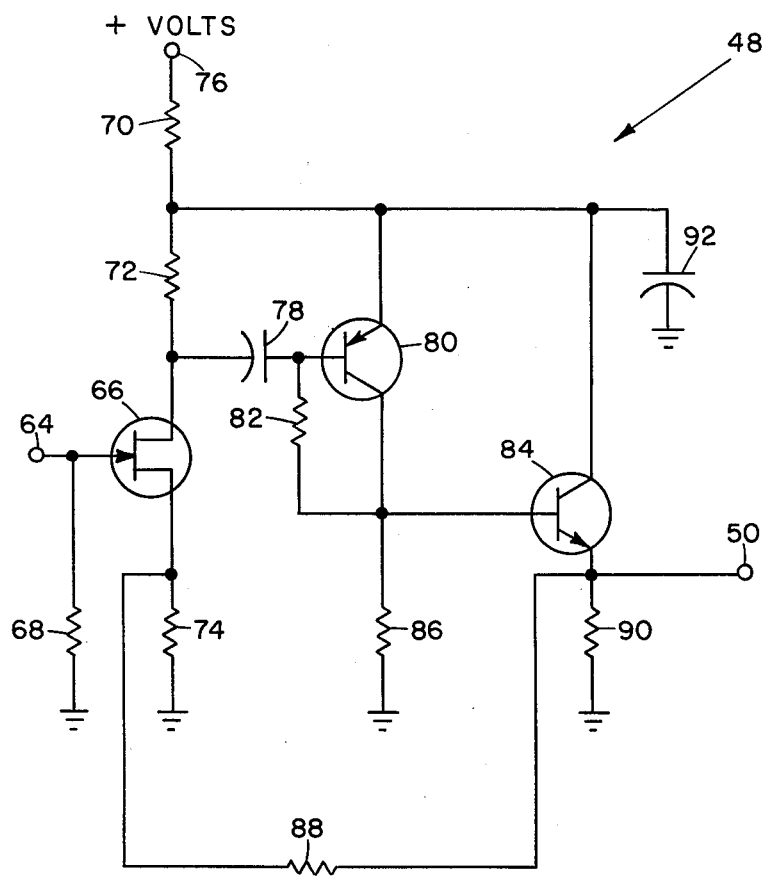
FIG. 5 is a schematic diagram of the preamplifier shown in FIG. 4.

Referring now to FIG. 5, a detailed schematic diagram of the preamplifier 48 is shown. The input terminal 64 receives the signal from the generating element 40 via output line 46. The signal from the generating element 40 is fed into a field effect transistor 66 across gate leak resistor 68. Drain load resistor 72 provides a path for the drain current of field effect transistor 66, and source bias resistor 74 completes the current path to ground. Voltage applied to the voltage terminal 76 could be over a range of DC voltages with +15 volts DC being typical. Resistor 70 is a decoupling resistor and resistor 74 provides for a feedback to the field effect transistor 66. The output of the field effect transistor 66 is capacitively coupled by capacitor 78 to a degeneratively biased bipolar transistor 80 connected as a high gain, collector loaded amplifier. Resistor 82 provides the necessary base bias current. The output of transistor 80, developed across collector load resistor 86, feeds to transistor 84. Transistor 84 acts as a bipolar emitter follower which provides isolation between loads connected to the output terminal 50 and the relatively high impedance collector circuit of the bipolar gain stage. Resistor 90 is the emitter load resistor for emitter follower transistor 84. A negative feedback from the emitter of transistor 84 through resistor 88 is provided to the field effect transistor 66. Capacitor 92 eliminates interaction between the preamplifier 48 through the voltage source connected to voltage terminal 76 and the remaining circuitry which may be operated from the same voltage source. Overall voltage gain of the preamplifier 48 is approximately 40 dB.

Figure 6:
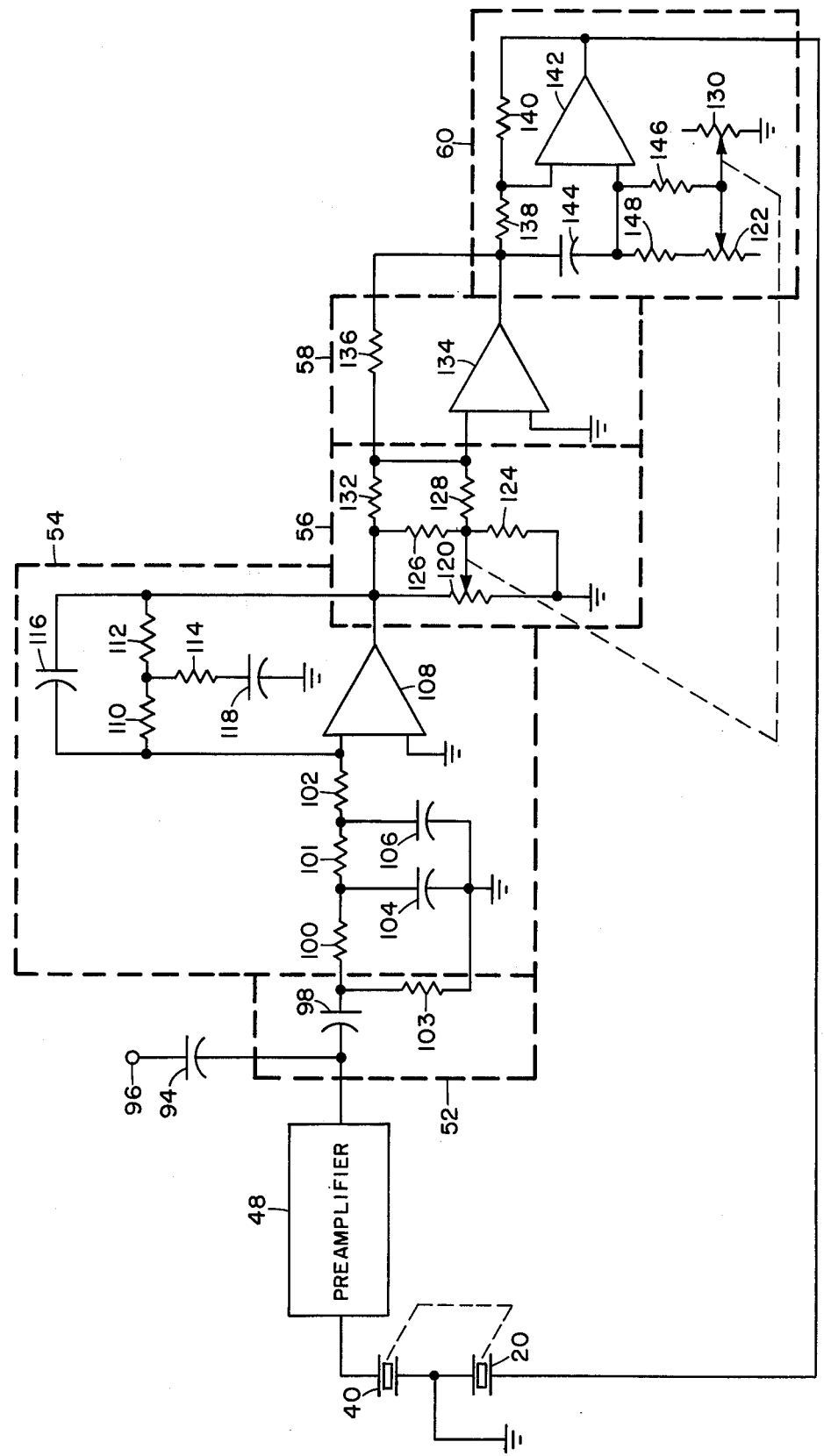
FIG. 6 is a schematic diagram of the electronics of an electronically tunable resonant accelerometer as shown in FIG. 4 and with a preamplifier as shown in FIG. 5.

Referring now to FIG. 6, a detailed schematic diagram for the circuit electronics (with the exception of the preamplifier previously described in conjunction with FIG. 5) is shown. The generating element 40 (which includes the second piezoelectric element 34 and the seismic mass 42) has an output signal that feeds into preamplifier 48. The output from the preamplifier 48 is connected through a blocking capacitor 94 to give an output signal at output terminal 96. Also, the output from the preamplifier 48 feeds into high pass filter 52 through coupling capacitor 98. The combination of series resistors 100, 101 and 102 in parallel with resistor 103 forms the resistive component of the high pass filter 52. The cutoff frequency of the high pass filter 52 is set at approximately 12% of the zero feedback resonant frequency of the accelerometer 10.

The series resistors 100, 101 and 102 provide a dual function as part of both the high pass filter 52 and the low pass filter 54. The low pass filter 54 is essentially a three pole Butterworth configuration cutting off at approximately 2.7 times the zero feedback resonant frequency of the accelerometer 10. The series resistors 100, 101 and 102 and the capacitors 104 and 106 form the input circuit for operational amplifier 108. Resistors 110, 112 and 114 in combination with capacitors 116 and 118 form a feedback circuit for operational amplifier 108. The input circuit of the operational amplifier 108 introduces two poles in the low pass filter transfer function, and the feedback circuit of operational amplifier 108 introduces two poles and one zero. One of the poles in the input circuit for the operational amplifier 108 is made to coincide with the zero in the feedback circuit thus eliminating one pole and zero from the transfer function of the low pass filter 54. The net result is a three pole, active, low pass filter 54. Time constants in the input and feedback circuits for the operational amplifier 108 are adjusted to achieve the three pole Butterworth response characteristic. Also, the input and feedback circuit resistances for operational amplifier 108 are adjusted so that the gain at low frequencies of the low pass filter 54 is unity.

Variable resistor 120 of gain control 56 is mechanically gang connected to variable resistor 130 of phase shifter 60. As the gain control 56 is tuned by variable resistor 120, variable resistor 130 also adjusts the phase response to minimize the possibility of oscillation of the accelerometer 10 as tuning is accomplished. Resistors 124, 126 and 128 alter the otherwise linear characteristics of variable resistor 120 to change its gain versus rotation curve in such a manner to enhance the phase compensation action of variable resistor 130 in phase shifter 60. Resistor 132 provides a bypass around the gain control 56 which also aids in the phase compensation action of variable resistor 130.

Operational amplifier 134 in inverter 58 inverts the signal received from the gain control 56. Resistor 136 provides feedback for operational amplifier 134.

The phase shifter 60, known as an "all-pass, phase-lead" circuit, includes input resistor 138 and feedback resistor 140 of operational amplifier 142. Capacitor 144 in conjunction with resistors 146 and 148 and variable resistors 122 and 130 develop a phase shifted input for operational amplifier 142. The frequency at which this circuit introduces 90° of phase shift is set by variable resistors 122 and 130. Resistor 146 limits the range of variable resistor 130, which helps provide for adjustment in phase compensation. By changing the setting of gang connected variable resistors 120 and 130, the gain of the feedback loop is set (which in turn sets resonant frequency), and appropriate phase compensation is introduced to maintain constant damping or quality factor (Q). Damping control is provided by variable resistor 122 which may be used to adjust system response from a highly over damped condition to a highly under damped condition. In the over damped condition, the resonant peak essentially disappears from the system frequency response, whereas in the highly under damped condition, the accelerometer will oscillate. System damping is inversely related to the quality factor (Q) of the resonance. Resistor 148 limits the range of variable resistor 122.

The output of operational amplifier 142 drives feedback element 20 which is mechanically coupled to the generating element 40. Since the feedback element 20 is mechanically coupled to the generating element 40, the feedback loop is complete.

The accelerometer 10 and the control circuit as shown in FIGS. 4, 5 and 6 have been explained in a configuration wherein the resonant frequency is tunable to frequencies on the high frequency side of the resonant frequency of the generating element 40 by itself. However, inverting feedback polarity and changing cutoff frequencies of high pass filter 52 and low pass filter 54, the resonant frequency would be tunable to frequencies on the low frequency side of the resonant frequency of generating element 40.

Since the piezoelectric elements 20 and 34 are capacitive, a good electrical connection with the piezoelectric elements 20 or 34 is not necessary and the bonding compound does not have to be conductive. All that is necessary is that an electrically conductive plate be in contact with each end of the respective piezoelectric elements 20 or 34. The plate may constitute any conductive material, such as the metallic base 12, the seismic mass 42 or the connecting discs 24 and 36.

ALTERNATIVE EMBODIMENT

The compression mode tunable resonant accelerometer as previously discussed is primarily a high frequency device. With typical piezoelectric materials, element dimensions become unwieldy for resonant frequencies below ten kilohertz (10 kHz). However, an alternative embodiment shown in FIG. 7 embodying a cantilever bender structure is better suited for low frequency operation. The cantilever bender element represented generally by reference numeral 150 is fabricated by bonding two thin slabs of piezoelectric material together, which piezoelectric slabs are represented by reference numerals 152 and 154. For a typical cantilever bender element, width of an individual slab forming either piezoelectric slab 152 or 154 is approximately twice its thickness, and length is usually in a range of 4 to 50 times its thickness. Thus, when the two piezoelectric slabs 152 and 154 are bonded together, a long slender bar of square cross-section is formed. The piezoelectric slabs 152 and 154 are polarized and connected together to take advantage of the traverse piezoelectric effect. Electrodes 156 and 158 are connected on opposite sides of a cantilever bender element 150 at the point of anchoring or applying motion. Therefore, any voltage generated across the cantilever bender element 150 due to applied motion will be sensed by the electrodes 156 and 158.

Figure 7:
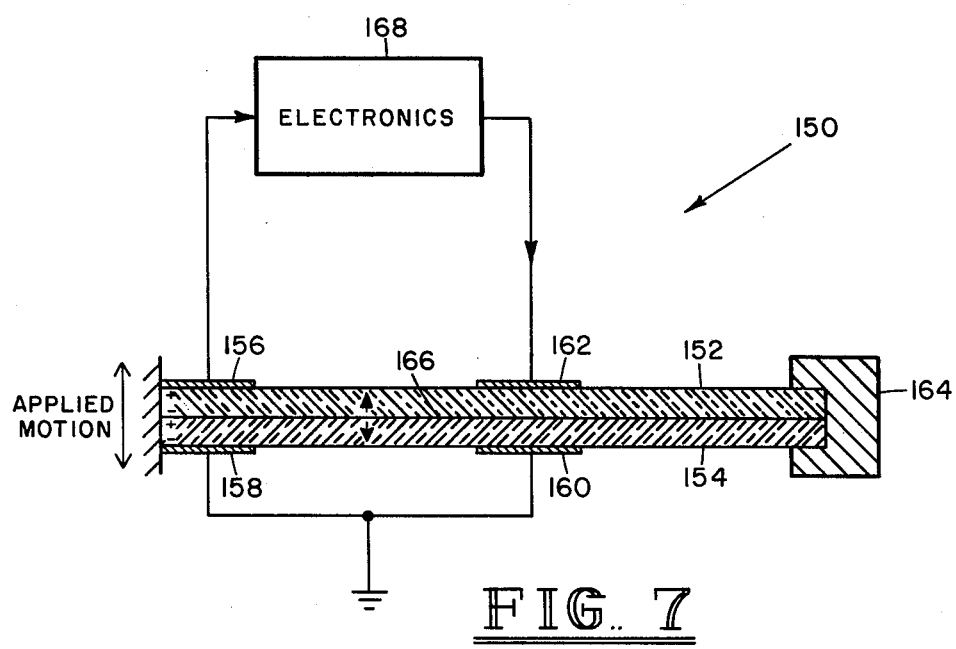
FIG. 7 is an alternative embodiment of an electronically tunable resonant accelerometer in the cantilever bender mode.

The cantilever bender element 150 may be either a series or parallel connection. Only the series connection will be discussed hereinbelow. To achieve a series connection, the piezoelectric slabs 152 and 154 are bonded together so that their polarization directions are opposing as shown in FIG. 7. The electrode 158 connected to piezoelectric slab 154 is grounded. In prior cantilever bender elements, the electrodes covered the entire top and bottom surfaces. In the present configuration, much of the electrode is removed with only a relatively narrow band being left on opposite faces of the cantilever bender element 150. However, the ground electrode could cover the entire bottom surface of piezoelectric slab 154 is desired, but in the present embodiment, electrode 158 and feedback electrode 160 are separate, but electrically connected together and to ground.

Since the electrical output of the cantilever bender element 150 is proportional to stress, and since the stress is greatest at the point of anchoring or applying motion of the cantilever bender element 150, electrodes 156 and 158 are connected nearest the point of applied motion to achieve maximum sensitivity. A feedback electrode 162 is located near the center of the cantilever bender element 150 and opposite grounded feedback electrode 160. Feedback electrode 162 is isolated from the generating element electrode 156 by the nonconducting piezoelectric slab 152.

A seismic mass 164 is added to the opposite end of the cantilever bender element 150 from the applied motion to reduce the resonant frequency and increase sensitivity. Any motion to be measured is applied to the point of anchoring, or the root, of the cantilever bender element 150 opposite the seismic mass 164.

Assume that applied motion is instantaneously upward. The inertial reaction force of the seismic mass 164 will be directed downward so that the cantilever bender element 150 will bend with piezoelectric slab 152 being in tension and piezoelectric slab 154 being in compression. The joint 166 where piezoelectric slab 152 is bonded to piezoelectric slab 154 is a neutral plane at zero stress. As a result of the stresses in cantilever bender element 150, a voltage will appear across electrodes 156 and 158. The voltage is received by electronics 168 which may be substantially the same as the electronics previously described in conjunction with FIGS. 4, 5 and 6. Output of the electronics 168 is connected to the feedback electrode 162 thus completing the feedback loop. Voltage appearing at the feedback electrode 162 will either aid or oppose prior movements by the cantilever bender element 150 depending upon the polarity of the feedback. However, because polarization of piezoelectric slab 152 is opposite the polarization of piezoelectric slab 154, if piezoelectric slab 152 expands, piezoelectric slab 154 will contract and vice versa. If the piezoelectric slab 152 contracts in response to voltage received through the feedback electrode 162, and piezoelectric slab 154 expands, the end of the cantilever bender element 150 having the seismic mass 164 thereon will have a tendency to bend upward. This has the apparent effect of stiffening the cantilever bender element 150 thus resulting in an increase in the resonant frequency.

In both the cantilever bender element 150 and the previously described compression mode accelerometer 10, reversal of feedback polarity has the opposite effect of tending to soften the spring constant of a mechanical equivalent system, thereby reducing resonant frequency. Cantilever bender elements 150, like the compression mode accelerometer 10, are distributed constant systems. Therefore, the cantilever bender element 150 will have multiple, non-harmonically related resonant frequencies similar to those of the compression mode accelerometer 10. Thus, the electronics 168 is very similar to that described for the compression mode accelerometer 10 in conjunction with FIGS. 4, 5 and 6. Constant functions in the responsive systems will be different to account for the different characteristics between the cantilever bender element 150 and the compression mode accelerometer 10.

I claim:

1. An electronically tunable resonant accelerometer for measuring applied reciprocating motion within a predetermined frequency range comprising:
   piezoelectric generating means for generating an output signal in response to said motion, said piezoelectric generating means having a resonant frequency;
   means for amplifying said output signal;
   feedback loop including means for adjusting gain of said feedback loop, and means for adjusting phase of a feedback signal from said amplifying means;
   piezoelectric feedback means mechanically coupled to said piezoelectric generating means and receiving said feedback signal from said feedback loop, said gain adjusting means and said phase adjusting means being adapted to vary said feedback signal and thereby tune said resonant frequency of said piezoelectric generating means over said predetermined frequency range;
   means for mounting said piezoelectric generating means and said feedback means and applying said reciprocating motion thereto.

2. The electronically tunable resonant accelerometer as given in claim 1 wherein said feedback loop comprises band pass means for allowing said feedback sigal within a band width about said resonant frequency to pass therethrough.

3. The electronically tunable resonant accelerometer as given in claim 2 wherein said band pass means includes high pass filter means for controlling a lower limit of said band width, and low pass filter means for controlling an upper limit of said band width.

4. The electronically tunable resonant accelerometer as given in claim 3 comprising means for damping said accelerometer to prevent unwanted oscillation of said accelerometer caused by said feedback signal and to vary a quality factor at resonance.

5. The electronically tunable resonant accelerometer as given in claim 4 wherein said amplifying means has a high input impedance and a low impedance output signal.

6. The electronically tunable resonant accelerometer as given in claim 4 further comprising inverter means in said feedback loop, said gain adjusting means being mechanically coupled to said phase adjusting means wherein varying of gain adjusting means simultaneously varies said phase adjusting means for said tuning of said resonant frequency over said frequency range.

7. The electronically tunable resonant accelerometer as given in claim 1 wherein said piezoelectric generating means is a first piezoelectric element and seismic mass, and said piezoelectric feedback means is a second piezoelectric element, said first and second piezoelectric elements operating in a compression mode.

8. The electronically tunable resonant accelerometer as given in claim 1 wherein said accelerometer is tuned on a high frequency side of said resonant frequency if said piezoelectric feedback menas is caused to change its dimensions in an opposite sense from a dimensional change of said piezoelectric generating means caused by said reciprocating motion, and on a low frequency side of said resonant frequency if said piezoelectric feedback means is caused to change its dimensions in a like sense to a dimensional change of said piezoelectric generating means caused by said reciprocating motion.

9. The electronically tunable resonant accelerometer as given in claim 1 wherein piezoelectric generating means and said feedback means are connected in a cantilever mode with two piezoelectric slabs being connected together along their longitudinal axis, said mounting means being on a first end of said two piezoelectric slabs.

10. The electronically tunable resonant accelerometer as given in claim 9 comprising first output electrode means connected to a first of said two piezoelectric slabs near said first end and second output electrode means connected to a second of said two piezoelectric slabs opposite said first output electrode means, said first and second output electrode means detecting said output signal, first feedback electrode means connected to said first piezoelectric slab at approximately the center of said longitudinal axis and second feedback electrode means connected to said second piezoelectric slab opposite said first feedback electrode means, said first and second feedback electrode means applying said feedback signal to said piezoelectric feedback means.

11. The electronically tunable resonant accelerometer as given in claim 10 comprising a seismic mass on a second end of said two piezoelectric slabs, said accelerometer being tunable on a high side of said resonant frequency if said piezoelectric feedback means is caused to change its dimensions in an opposite sense from a dimensional change of said piezoelectric generating means caused by said reciprocating motion, and on a low frequency side of said resonant frequency if said piezoelectric feedback means is caused to change its dimensions in a like sense to a dimensional change of said piezoelectric generating means caused by said reciprocating motion.

12. A method of tuning resonant frequency of an accelerometer over a frequency range consisting of the following steps:
mechanically coupling a first piezoelectric means to a second piezoelectric means;
amplifying an output signal generated by said first piezoelectric means in response to motion thereof;
connecting a feedback signal from said output signal through a feedback loop to said second piezoelectric means;
adjusting gain of said feedback loop and simultaneously varying phase of said feedback signal through said feedback loop;
said adjusting gain and varying phase tuning said resonant frequency over said frequency range.

13. The method of tuning resonant frequency of an accelerometer as recited in claim 12 includes an additional step of changing damping of said feedback loop.

14. The method of tuning resonant frequency of an accelerometer as recited in claim 13 includes a step of passing said feedback signal through a band pass filter, said band pass filter setting said frequency range.

15. The method of tuning resonant frequency of an accelerometer as recited in claim 14 wherein said frequency range is on a high frequency side of said resonant frequency if said piezoelectric feedback means is caused to change its dimensions in an opposite sense from a dimensional change of said piezoelectric generating means caused by said reciprocating motion.

16. The method of tuning resonant frequency of an accelerometer as recited in claim 14 wherein said frequency range is on a low frequency side of said resonant frequency if said piezoelectric feedback means is caused to change its dimensions in a like sense to a dimensional change of said piezoelectric generating means caused by said reciprocating motion.

* * * * *